United States Patent [19]

Boag et al.

[11] 3,990,973
[45] Nov. 9, 1976

[54] APPARATUS FOR MEASURING ULTRAFILTRATION RATE

[75] Inventors: James T. Boag, Conifer; Luke Richard Schmieder, Lakewood, both of Colo.

[73] Assignee: Cobe Laboratories, Inc., Lakewood, Colo.

[22] Filed: Nov. 4, 1974

[21] Appl. No.: 520,337

[52] U.S. Cl. .............................. 210/87; 210/96 M; 210/321 B
[51] Int. Cl.² ......................................... B01D 31/00
[58] Field of Search .................. 210/62, 22, 85, 87, 210/96, 321

[56] References Cited
UNITED STATES PATENTS

| | | | |
|---|---|---|---|
| 3,416,664 | 12/1968 | Kumme et al. | 210/321 X |
| 3,441,136 | 4/1969 | Serfass et al. | 210/96 X |
| 3,527,700 | 9/1970 | Goldhaber | 210/321 X |
| 3,669,880 | 6/1972 | Marahtz et al. | 210/321 X |
| 3,795,318 | 3/1974 | Crane et al. | 210/321 |
| 3,844,940 | 10/1974 | Kopf et al. | 210/321 X |

*Primary Examiner*—Frank A. Spear, Jr.
*Attorney, Agent, or Firm*—Reising, Ethington, Barnard

[57] ABSTRACT

A system is disclosed for measuring the ultrafiltration rate in an artificial kidney. The system comprises a flow rate meter connected with the outlet of the dialyzer, means for placing the flow control system in bypass so that the dialysate flow is diverted around the dialyzer, and means for maintaining the static pressure of dialysate in the dialyzer during bypass at a value equal to the average of the dynamic pressure prior to bypass. The flow rate indicated by the meter during the bypass interval is equal to the rate of ultrafiltrate flow through the dialyzing medium. Preferably, the pressure in the dialyzer during bypass is maintained by a negative pressure regulating means which responds to the average value of dialysate pressure in the dialyzer during both the run and bypass operations.

9 Claims, 2 Drawing Figures

APPARATUS FOR MEASURING ULTRAFILTRATION RATE

This invention relates to artificial kidneys, more particularly, it relates to apparatus for measuring the rate of flow of ultrafiltrate through the dialyzing medium.

By hemodialysis in an artificial kidney, the water and certain waste products are removed from the blood of the patient. The process is carried out in a dialyzer which includes a flow path for the patient's blood separated by a dialyzing medium, in the form of a semipermeable membrane, from a flow path for a liquid dialysate. Most of the waste removal occurs by mass transfer through the membrane and water removal occurs by ultrafiltration through the membrane. The rate of ultrafiltration is controlled by causing the liquid dialysate to flow through the dialyzer at a controlled negative pressure, i.e. a pressure value less than atmospheric. The ultrafiltration rate is of great importance in the hemodialysis treatment and should by carefully controlled at a value which meets the needs of the individual patient. Although ultrafiltration rate has long been regarded as one of the principal variables in hemodialysis treatment, there has not been a satisfactory technique for measurement of ultrafiltration rate during the course of hemodialysis treatment. Heretofore, the predominant measurement technique has depended upon weighing of the patient at time intervals during treatment. This technique provides the needed information only after the treatment has been in progress for a substantial time. There has been a long standing need for instrumentation to provide measurement of ultrafiltration, preferably with the measurement and readout thereof being coincident in time with the rate being measured.

According to this invention, ultrafiltration rate can be measured at any time during the hemodialysis treatment and a readout is provided concurrently with the measurement. This is accomplished, in general, by putting the dialysis machine in "bypass", maintaining the dialysate pressure in the dialyzer, and measuring the flow from the dialysate outlet. Preferably, the flow rate is measured with a meter connected to the dialyzer; the apparatus includes means for interrupting the dialysate flow to the dialyzer inlet and for diverting fluid flow from the dialyzer outlet to the meter inlet. To assure the accuracy of the measurement, means are provided to maintain the dialysate pressure in the dialyzer during measurement at a value equal to the average value of the dynamic pressure in the dialyzer during dialysate flow therethrough. Further, it is preferred to maintain the pressure of the dialysate in the dialyzer during measurement by means which divert the dialysate flow through a dialyzer bypass flow path but which maintain fluid communication with the outlet of the dialyzer. Additionally, the means for maintaining the pressure of the dialysate in the dialyzer also preferably includes a negative pressure regulating system. The measurement accuracy by the flow rate meter is further enhanced by negative pressure regulating means which includes means for sensing the average value of the dialysate pressure in the dialyzer and regulating the value thereof.

A more complete understanding of this invention may be obtained from the detailed description that follows, taken with the accompanying drawings in which.

Figure 1:
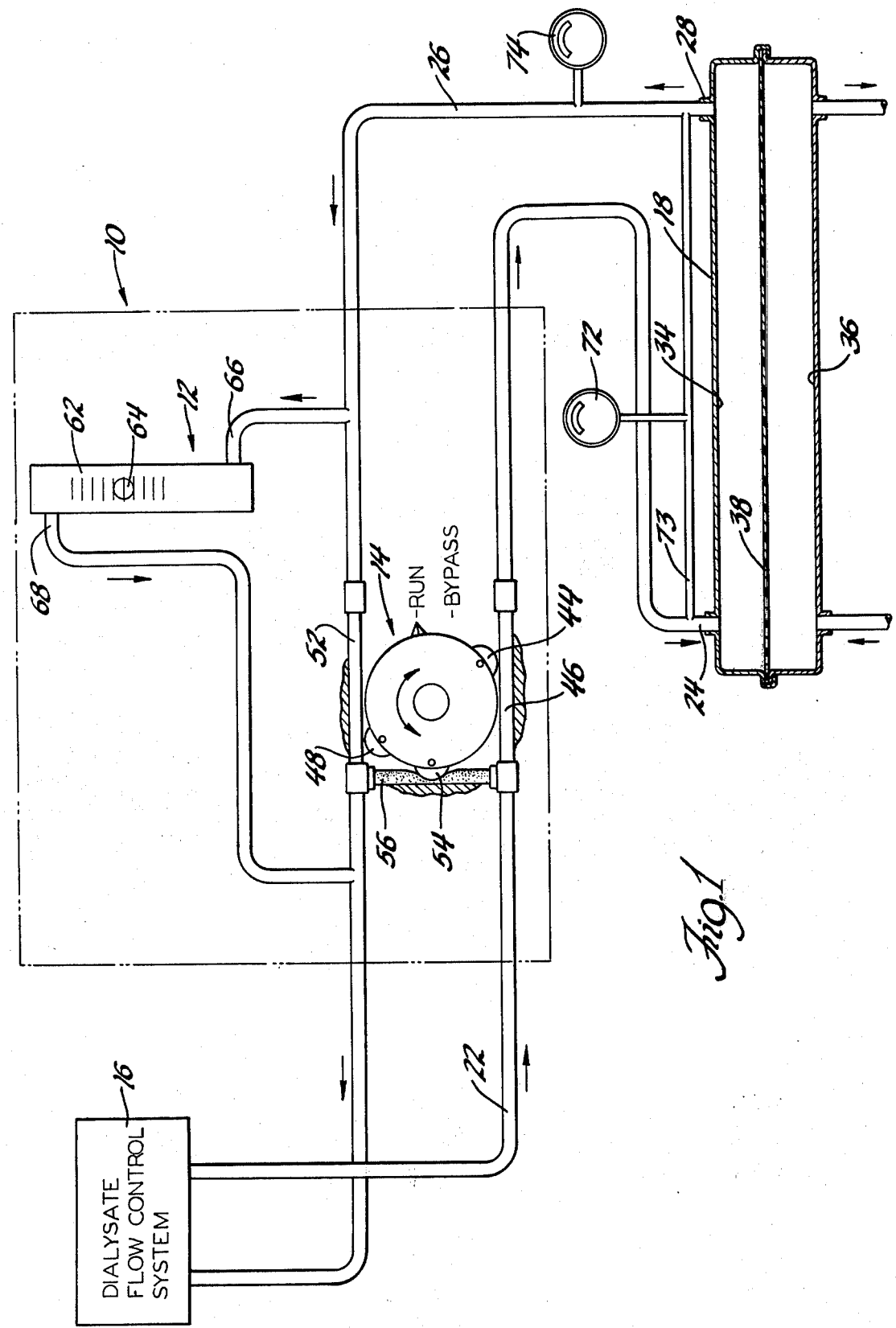
FIG. 1 is a diagram of the ultrafiltration rate meter.

Referring now to the drawings, an illustrative embodiment of the invention is shown in conjunction with an artificial kidney for measuring the rate of flow of ultrafiltrate through the membrane of the dialyzer. As used herein, the term ultrafiltrate means the waste products and other material which, by action of the dialyzer of an artificial kidney, is transferred from the blood fow path in the dialyzer through the membrane thereof to the dialysate flow path in the dialyzer.

As shown in FIG. 1, the ultrafiltration rate (UFR) meter 10 comprises, in general, a flow rate meter 12 and valve means 14 interposed in the dialysate flow path of an artificial kidney. The artificial kidney comprises a flow control system 16 for the dialysate, the flow control system being of conventional design. THe artificial kidney also includes a dialyzer 18, of conventional design, and the dialysate flow path includes a supply conduit 22 extending from a dialysate source in the flow control system 16 to the dialysate inlet 24 of the dialyzer 18. The flow path also includes an effluent conduit 26 extending from the outlet 28 of the dialyzer to a drain in the flow control system. The dialyzer 18, shown diagrammatically in FIG. 1, includes a dialysate chamber 34 and a blood chamber 36 with the chambers being separated by a dialyzing membrane 38. The blood flow path of the artificial kidney includes the chamber 36 of the dialyzer which includes an inlet and an outlet as indicated.

When the artificial kidney is in operation, the flow control system 16 delivers the liquid dialysate through the supply conduit 22 under controlled conditions to the inlet 24 of the dialyzer. The effluent from the dialyzer includes the liquid dialysate along with the ultrafiltrate and flows from the outlet of the dialyzer through the effluent conduit to the flow control system. The typical flow control system, originates with a water supply and extends through heating means for warming the dialysate to body temperature, degasing means for removing dissolved air, a mixer for mixing concentrated dialysate solution with incoming supply water, and a negative pressure control system for maintaining the dialysate at a negative pressure in the dialyzer during the dialysate flow therethrough. The conventional artificial kidney also includes a bypass valve interposed in the dialysate flow path to controllably divert the dialysate flow around the dialyzer for various reasons; for example, when the temperature or the concentration of the dialysate is not at the proper value. This bypass valve may take a wide variety of forms, in practice, and, as will be appreciated from the description that follows, the bypass valve may be utilized in accordance with this invention as the valve means for initiation of the measurement of UFR, provided it performs the requisite functions as will be described below.

In the UFR meter 10, the valve means 14 is actuable between two positions which are denominated the "run" position and the "bypass" position. In the "run" position the dialysate is caused to flow through the dialyzer and in the "bypass" position the dialysate flow path is diverted around the dialyzer. The valve means 14 is used in the implementation of the subject invention to initiate and terminate the measurement of UFR; for convenience, however, the valve means 14 will herein be called the "bypass" valve, since, in addition to the measurement function, it also performs the conventional bypass function in the dialysate flow system, as discussed above.

The bypass valve 14 may be constructed as a roller type valve which is shown diagrammatically in FIG. 1. This valve comprises a rotor 42 which is manually rotatable between a "run" position and a "bypass" position. The rotor 42 carries a roller 44 which coacts with a flexible conduit portion or valve passage 46 which forms a part of the supply conduit 22. The rotor also carries a roller 48 which coacts with a flexible conduit portion or valve passage 52 forming a part of the effluent conduit 26. Additionally, the rotor carries a roller 54 which coacts with a flexible conduit portion or bypass passage 56 connected between the supply and effluent conduits in parallel with the dialyzer to bypass the same. With the bypass valve 14 in the "run" position as shown, the roller 14 engages the bypass passage 56 and flattens it against a reaction member to maintain the passage closed. In this position the rollers 44 and 48 are out of engagement with the passages 46 and 52 and, hence, the flow path through the dialyzer is open. When the valve is actuated to the "bypass" position by clockwise rotation, the rollers 46 and 48 are operative to close the passages 46 and 54 and the dialyzer is effectively isolated from the dialysate source. However, the roller 54 is moved out of engagement with the passage 56 which is thereby opened and constitutes a passage for conducting the dialysate flow from the supply conduit 22 to the effluent conduit 26.

The flow rate meter 12, which is switched in and out of operation by the bypass valve 14, is of conventional construction and illustrated diagrammatically in FIG. 1. The meter 12 is selected to have a measurement range consistent with the low flow rates of ultrafiltration, such measurement range extending, for example, from zero to 15 milliliters per minute. The meter 12 may be of the type known as a "rotometer" which comprises a vertical, graduated flow chamber 62 containing a float 64. The meter 12 has an inlet 66 near the bottom of the chamber which is connected to the effluent conduit between the dialyzer outlet and the valve passage 52. The meter 12 has an outlet near the top of the chamber which is connected with the effluent conduit at a point downstream from the valve passages 52 and 56. As is well known, the float 64 will be suspended in the column of liquid in the meter chamber 62 at a height corresponding to the rate of flow. The chamber 62 is suitably calibrated in kilograms per hour.

In order to obtain an accurate measure of flow rate of the ultrafiltrate, the same flow rate is continued during the measurement period (while the valve 14 is in "bypass") as existed during the immediately preceding treatment period (while the valve 14 is in "run"). Accordingly, it is important to maintain the same pressure of the dialysate in the chamber 34 of the dialyzer during both "run" and "bypass" modes of operation. For this purpose, the supply conduit 22, is in effect, disconnected from the dialyzer and the dialysate flow therethrough is terminated. At the same time the valve 14 closes the effluent conduit at the passage 52. The chamber 34 in the dialyzer, of course, remains filled with dialysate in this "bypass" condition but the dialysate flow is terminated and hence, the dialysate becomes static; provided that the meter connection does not allow the dialysate pressure to change, the static pressure becomes equal to the average of the dynamic pressure which existed just prior to "bypass". The dialysate pressure will quickly reach equilibrium in the chamber 34 and the rate of ultrafiltration will continue at the same value as during the "run" mode. The ultrafiltrate entering the dialysate chamber will, of course, increase the liquid volume (being the mixture of dialysate and ultrafiltrate) and will produce a flow through the meter 12 at a flow rate equal to the rate of ultrafiltration in the dialyzer.

In order to prevent the meter connection from allowing a change of dialysate pressure during the measurement interval, a special interconnection is made with the pressure control system. As illustrated in FIG. 1, this includes the connection of the outlet 68 of the meter 12 through the effluent conduit, and hence to the dialysate flow control system. This connection along with the bypass flow of dialysate through the bypass passage 56, permits the pressure at the outlet 68 of the meter to be adjusted to a value during "bypass" operation which will hold the static pressure of the dialysate in the dialyzer during "bypass" at the same value as the average value therein during "run". If the dialysate flow control system 16 is of the type which is provided with a manually controlled negative pressure regulation system, it is desirable to observe the average value of dynamic pressure in the chamber 34 during "run" before the switchover to "bypass". The reading of average dynamic pressure in the dialyzer may be provided, for example, by a pressure gauge 72 connected to the midpoint of a shunt passage 73 which extends between the inlet and outlet of the dialyzer. Then the manual control device for negative pressure adjustment should be adjusted so that the static pressure at the dialyzer outlet 28, as observed on a pressure gauge 74, is equal to the previously noted average dynamic pressure.

Figure 2:
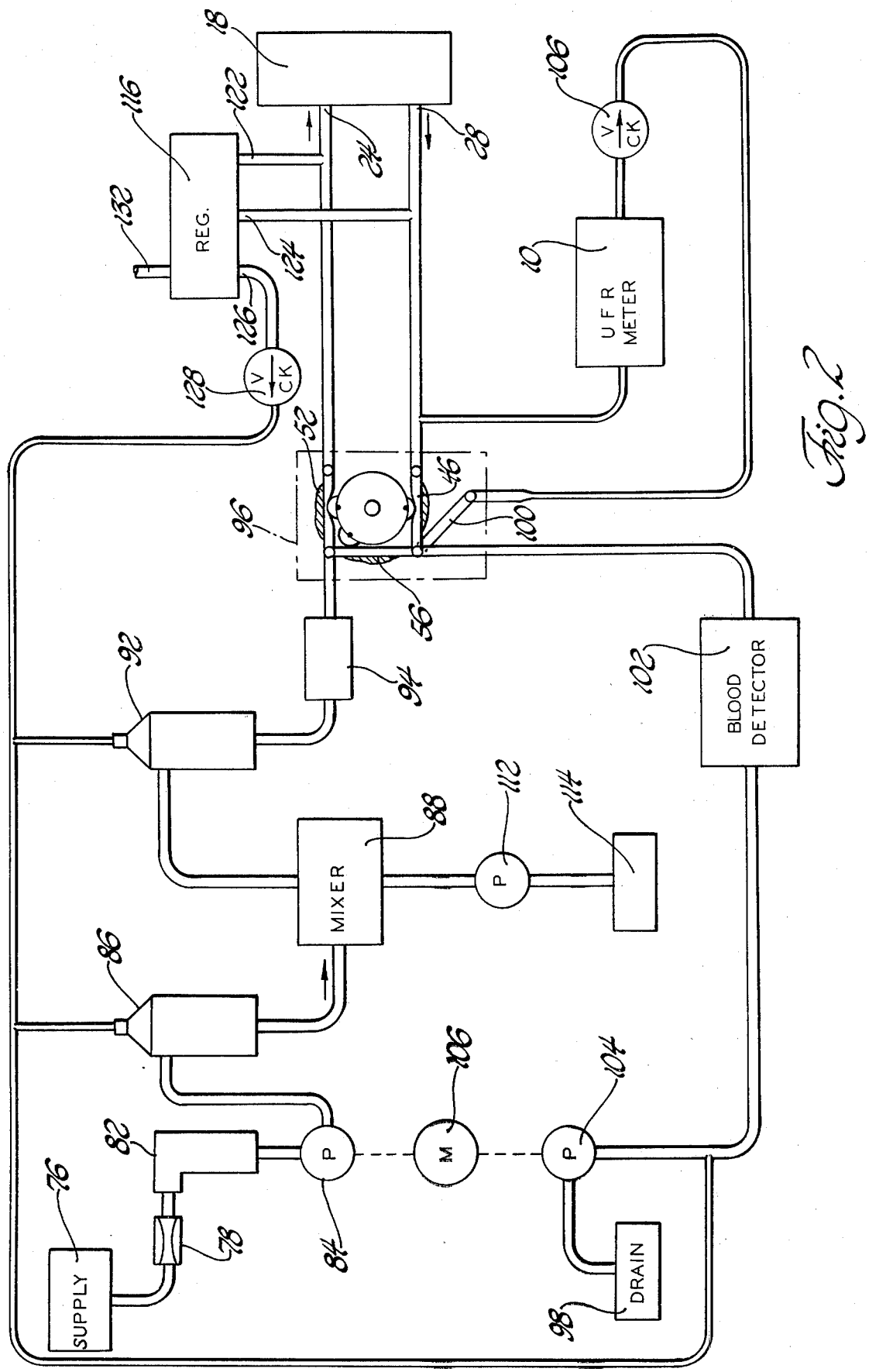
FIG. 2 is a diagram of a dialysate flow control system embodying the ultrafiltration rate meter of this invention.

While the subject invention is useful for measuring ultrafiltration rate in an artificial kidney with any form of dialysate flow control system, it is especially advantageous in conjunction with the dialysate flow control system as illustrated in FIG. 2. This dialysate flow control system, with automatic negative pressure regulation and with negative pressure degassing, is disclosed and claimed in copending patent application Ser. No. 520,336 filed on even date herewith by Robert White et al and assigned to the same assignee as this invention. The aforementioned patent application also discloses a particular selector valve (bypass valve) which is especially advantageous in conjunction with the negative pressure control system set forth therein and the UFR meter of this invention.

Referring now to FIG. 2, the dialysate flow control system comprises a water supply source 76 and a dialysate supply conduit extending therefrom and defining a flow path to the inlet of the dialyzer 18. The supply conduit, in general, includes a flow controller 78, a heater 82, a first stage suction pump 84, a first deaerator 86 and a mixer 88 for admitting a controlled quantity of concentrated dialysate solution to the dialysate flow path. The supply conduit additionally comprises a second deaerator 92, a conductivity monitoring cell 94 and a passage through a bypass valve 96, which is connected to the inlet of the dialyzer 18. The dialysate flow control system also comprises an effluent conduit which defines a flow path extending from the outlet of the dialyzer 18 to a liquid drain 98. This effluent conduit includes a passage through the selector valve 96, a blood leak detector 102 and a second stage suction pump 104. The pumps 84 and 104 are positive displacement pumps of similar characteristics and are driven by a common motor 106. The dialysate flow control system also comprises a negative pressure regulator 116. The ultrafiltration rate meter 10 has its inlet connected with the outlet of the dialyzer and its outlet connected through a check valve 106 to a meter passage 100 in the valve 96. The meter passage enters the effluent conduit downstream of the valve element therein.

The negative pressure dialysate flow control system operates in the following manner. The supply water from the source 76 is delivered at a positive pressure of several hundred torr. With the pumps 84 and 104 in operation and the valve 96 in the "run" position, continuous liquid flow will be produced from the supply to the drain. The flow controller 78 produces a large pressure drop and the pressure decreases from a high positive value to a relatively low negative value, i.e. below atmospheric. The negative pressure is produced by reason of the pump 84. The pump 84 reduces the pressure at the downstream side of the flow controller 78 to a negative value because the pump 84 is a positive displacement pump with a capacity greater than the flow rate which the flow controller can sustain at the pressure drop thereacross. The pump 84, of course, produces a pressure rise between its inlet and outlet but, due to the action of the pump 104, the pressure does not rise above atmospheric. The negative pressure at the outlet of pump 84 is maintained because the pump 104 produces a greater flow rate than the pump 84. Between the outlet of pump 84 and the inlet of the dialyzer 18, the flow path includes a passage 52 of the bypass valve 96. From the outlet of the dialyzer the flow path extends through passage 46 of the bypass valve 96. The dialysate pressure reaches the most negative value between the pumps at the inlet of pump 104. The pump 104 produces a pressure rise which is limited by the fluid pressure of the drain 98 encountered at the pump outlet.

Deaeration of the dialysate is accomplished in the flow path with the aid of negative pressure and dialysate heating at particular points in the flow path. The heater 82 is disposed in the flow path between the flow controller and the pump 84 and functions in a conventional manner to increase the temperature of the water to approximately the body temperature of the patient. Both the decrease in pressure and the increase in temperature tend to cause the dissolved air in the water to come out of solution in the form of minute bubbles entrained in the water. The deaeration of the dialysate in the flow path occurs for the most part between the heater 18 and the pump 84. This deaeration process includes releasing of the dissolved air in the form of minute bubbles of air entrained in the liquid and the combining of the minute bubbles into larger bubbles which is a continuous process between the heater and the pump inlet. Thus the pump 84 pumps the liquid with the entrained air to a higher pressure through the first accumulator 86. The accumulator is provided with a vent or air outlet at its upper extremity, the outlet being connected through a discharge conduit 108 to an "air dump" point 110 downstream of the accumulator 86 and upstream of the second stage pump 104. The accumulator 86 is provided with a float valve which is adapted to seat against a valve seat at the air outlet when the liquid in the tank rises above a predetermined level. When the liquid is below the predetermined level the vent is open and the accumulated air above the liquid will be vented through the conduit to the dump point 110.

The deaerated water from the accumulator 86 flows through the mixer 88 which injects a relatively small volume of concentrated liquid dialysate into the stream of water. The mixer 88 is suitably of conventional construction and the "concentrate" is supplied thereto from the source 112 by a pump 114. The pump 114 is adapted to meter an accurately controlled volume of concentrate into the mixer and is suitably of the peristaltic type. Since this type of pump tends to produce a non-homogeneous mixture of the concentrate and water, by reason of the periodic injections of concentrate, it is desirable to provide for additional mixing so that the concentration of the dialysate is uniform when it reaches the dialyzer. This is the principal purpose of the second accumulator 92; secondarily, this accumulator separates some additional quantity of air from the liquid dialysate. The accumulator 92 is suitably of the same construction as accumulator 88 and the air outlet is connected through the discharge conduit 108 to the air dump point 110.

The liquid dialysate leaving the accumulator 88 is conditioned for entry into the dialyzer 18. The system is suitably provided with an automatic control loop for regulating the concentration of the dialysate and the temperature thereof. For this purpose, the monitor device 94 is interposed in the flow path and is adapted to produce an electrical signal indicative of conductivity of the dialysate for use in the concentrate control loop (not shown) which controls the pump 112. The monitor device 94 also includes a temperature sensor which produces an electrical signal indicative of dialysate temperature for the temperature control loop (not shown) which controls the heater 82. The control loops alluded to above may be of conventional design and are commonly used in artificial kidney machines. The location of the monitor device 94 after deaeration of the dialysate ensures that the conductivity measurement for concentration control will be unaffected by dissolved or entrained air in the liquid.

Although the bypass valve 96 may be of conventional design, a preferred valve structure which is especially advantageous for use in conjunction with the ultrafiltration rate meter 10 is disclosed in detail in the aforementioned patent application Ser. No. 520,336.

The pressure of the dialysate in the dialyzer is automatically regulated to maintain the predetermined value which is manually adjustable according to the needs of the individual patient. The regulating means comprises a regulator 116 which is preferably of the structure shown in the aforementioned patent application, Ser. No. 520,336. The regulator is provided with a control liquid inlet 122 connected with the dialyzer inlet and is provided with a control liquid outlet 124 connected with the dialyzer outlet. Additionally, the regulator is provided with a controlled fluid outlet 126 which is connected through a check valve 128 to the air dump point 110. The controlled fluid, preferably ambient air at atmospheric pressure, is supplied to the regulator through a controlled fluid inlet 132.

The regulator 116 is operative to regulate the pressure of the dialysate in the dialyzer in accordance with a manually selected value, as is fully described in said patent application Ser. No. 520,336. The regulator functions in the manner of an adjustable relief valve and when the negative pressure of the control liquid becomes excessively large, controlled fluid will be admitted through the regulator to the air dump point 110 to relieve the suction at the intake of the pump 104. As shown in FIG. 2, with the control inlet 122 and the control outlet 124 connected to the dialyzer inlet and outlet respectively, the pressure sampled or sensed by the regulator will be equal to the average value of pressure in the dialyzer, i.e. it will have a value midway between the inlet and outlet pressures of the dialyzer. The controlled fluid inlet 132 is in communication with the ambient air at atmospheric pressure, and, as previously noted, the controlled fluid outlet 126 is connected with the air dump point 110 through the check valve 128.

The second stage pump 104 operates at a flow rate which will continuously tend to increase the negative pressure in the dialyzer to a value greater than the set value. When this excess value is reached the regulator admits air from the atmosphere through the controlled fluid inlet 132, the outlet 126 and the check valve 128 to the air dump point 110. A quantity of air is admitted to the intake of pump 104 sufficient to decrease the negative pressure in the dialyzer to allow the regulator to stop admitting air. This regulating action is repetitive during operation of the system, with the valve opening and closing occurring at a relatively high rate so that the pressure value oscillates or "hunts" about the regulated value through a very small range of deviation.

The pressure regulating system, as just described, is operative to respond to the dialyzer pressure during the "run" mode and also during the "bypass" mode of operation of the system. The bypass valve 96, as described above, disconnects the inlet of the dialyzer from the dialysate flow path during the "bypass" mode of operation; it also disconnects the outlet of the dialyzer from direct connection with the flow path by closing the return passage 52. However, the outlet of the dialyzer remains in fluid communication with the effluent conduit at a point downstream of passage 46 through the ultrafiltration rate meter 10, the check valve 106 and the meter passage 100. The outlet 124 of the regulator 116 is thereby connected through the ultrafiltration rate meter to the effluent conduit at the outlet of the valve passage 46. Since the pressure value at this point is communicated to the regulator 116 (during both "run" and "bypass"), the regulator, during "bypass", will operate to change the dynamic pressure in the bypass flow path until the pressure at the outlet of the valve passage 46 becomes equal to the average dynamic pressure in the dialyzer during "run". Accordingly, the ultrafiltration rate will remain the same in the "bypass" mode, and the volume of flow through the meter 10 will be due solely to the ultrafiltrate which permeates the dialyzer member. The ultrafiltration rate is therefore subject to accurate measurement by momentary switching of the bypass valve 96 from "run" to "bypass". The accuracy of this measurement is enhanced by reason of using the average dynamic pressure in the dialyzer as the control pressure in the regulator. This ensures that the dialysate flow through the meter occurs at the same pressure as the pressure in the dialyzer because, during "bypass", the regulator holds the pressure at the outlet of passage 46, and hence at the outlet of meter passage 100, at the same pressure as that in the dialyzer. If pressure other than the average value were to be sampled or sensed at the dialyzer for regulation purposes, there would be a change of pressure at the outlet of meter passage 100 upon switching to "bypass". This would affect the ultrafiltration rate and the reading of the UFR meter would not represent the rate of ultrafiltration which is produced during operation.

Although the description of this invention has been given with reference to a particular embodiment it is not to be construed in a limiting sense. Many variations and modifications will now occur to those skilled in the art. For a definition of the invention reference is made to the appended claims.

The embodiments of the present invention in which an exclusive property or privilege is claimed are defined as follows:

1. In an artificial kidney, apparatus for measuring the ultrafiltrate flow through the dialyzing medium of a dialyzer comprising a flow path for dialysate adapted to be connected to the dialyzer inlet and to the dialyzer outlet, a meter having an inlet adapted to be connected with the dialyzer outlet, means in the flow path for interrupting the dialysate flow to the dialyzer inlet and for diverting the flow from said dialyzer outlet to said meter inlet whereby said meter measures the ultrafiltrate flow, and means for maintaining the pressure of the dialysate in the dialyzer at a value substantially equal to the average value of the dynamic pressure in the dialyzer prior to interruption of the dialysate flow to the dialyzer.

2. The invention as defined in claim 1 wherein said means for maintaining the pressure of the dialysate includes means for diverting the dialysate flow from a first point in the dialysate flow path upstream of the dialyzer inlet to a second point in the dialysate flow path downstream of the meter inlet and wherein said meter has an outlet connected to the dialysate flow path at said second point.

3. The invention as defined in claim 2 wherein said means for maintaining the pressure of the dialysate includes a negative pressure regulating system connected with said flow path.

4. The invention as defined in claim 3 wherein said negative pressure regulating means includes means for sensing the average value of the dialysate pressure in the dialyzer and regulating the value thereof.

5. The invention as defined in claim 2 wherein said meter is a flow rate meter.

6. In an artificial kidney, apparatus for measuring the flow rate of ultrafiltrate through the dialyzing medium of a dialyzer comprising: blood flow means adapted to be connected with the blood inlet and outlet of the dialyzer, a dialysate supply conduit and a dialysate effluent conduit adapted to be connected, respectively, to the dialysate inlet and outlet of the dialyzer, a flow rate meter having a meter inlet and a meter outlet connected with the effluent conduit, the meter outlet being connected with the effluent conduit downstream of the meter inlet, valve means including a first valve element in said supply conduit and actuable from an open position to a closed position for interrupting the flow to said dialyzer and a second valve element in said effluent conduit and actuable from an open position to a closed position for interrupting the flow therethrough between said meter inlet and meter outlet, and means for maintaining the pressure of the dialysate in the dialyzer at a value substantially equal to the average value of the dynamic pressure in the dialyzer prior to actuation of said valve elements, whereby said meter indicates the flow rate of ultrafiltrate when said valve elements are actuated.

7. The invention as defined in claim 6 wherein said means for maintaining the pressure of the dialysate includes means for diverting the dialysate flow from the supply conduit at a first point upstream of the first valve element to the effluent conduit at a point downstream of said second valve element.

8. The invention as defined in claim 7 wherein said means for maintaining the pressure of the dialysate includes a negative pressure regulating system connected with said conduits.

9. The invention as defined in claim 8 wherein said negative pressure regulating means includes means for sensing the average value of the dialysate pressure in the dialyzer and regulating the value thereof.

* * * * *